(12) United States Patent
Allred

(10) Patent No.: US 9,855,035 B2
(45) Date of Patent: Jan. 2, 2018

(54) GRASPING APPARATUSES FOR HOLDING NEEDLES AND RELATED METHODS

(71) Applicant: Seton Healthcare Family, Austin, TX (US)

(72) Inventor: James Allred, Austin, TX (US)

(73) Assignee: SETON HEALTHCARE FAMILY, Austin, TX (US)

( * ) Notice: Subject to any disclaimer, the term of this patent is extended or adjusted under 35 U.S.C. 154(b) by 110 days.

(21) Appl. No.: 14/694,323

(22) Filed: Apr. 23, 2015

(65) Prior Publication Data

US 2016/0051254 A1 Feb. 25, 2016

Related U.S. Application Data

(60) Provisional application No. 62/040,003, filed on Aug. 21, 2014.

(51) Int. Cl.
*A61B 17/04* (2006.01)
*A61B 17/12* (2006.01)
(Continued)

(52) U.S. Cl.
CPC ........ *A61B 17/062* (2013.01); *A61B 17/2841* (2013.01); *A61B 2017/00424* (2013.01);
(Continued)

(58) Field of Classification Search
CPC .......... A61B 17/062; A61B 2017/2837; A61B 17/0469; A61B 17/0483; A61B 17/12013;
(Continued)

(56) References Cited

U.S. PATENT DOCUMENTS

| 848,966 A | * | 4/1907 | Carlson | .................. B26B 13/16 30/232 |
| 1,266,456 A | | 5/1918 | Greeley | ........................ 606/147 |

(Continued)

FOREIGN PATENT DOCUMENTS

| EP | 0571057 | 5/1993 |
| EP | 0690700 | 5/1998 |

(Continued)

OTHER PUBLICATIONS

ORsupply, http://www.orsupply.com/medical/category/Surgical-%C2%AD%E2%80%90Instruments/872/category/Surgical-%C2%AD%E2%80%90Needle-%C2%AD%E2%80%90Holders/902, Accessed: Sep. 25, 2015.

(Continued)

*Primary Examiner* — Katherine M Shi
(74) *Attorney, Agent, or Firm* — Norton Rose Fulbright US LLP

(57) ABSTRACT

This disclosure includes needle holders and related methods. Some holders use or include an elongated handle having a proximal portion and a distal portion, a first jaw member coupled to the distal portion of the handle, a second jaw member pivotally coupled to the first jaw member, and a lever pivotally coupled to the handle and coupled to the second jaw member such that the lever can be actuated by a user's thumb to selectively open and close the jaw members. In some holders, the handle extends proximally beyond the lever such that the lever can be actuated by the user's thumb to selectively open and close the jaw members while the handle is grasped within the user's hand. In some holders, the handle is defined by an elongated housing defining an interior volume configured to receive at least a portion of the lever when the jaw members are closed.

5 Claims, 9 Drawing Sheets

(51) Int. Cl.
*A61B 17/062* (2006.01)
*A61B 17/00* (2006.01)
*A61B 17/28* (2006.01)

(52) U.S. Cl.
CPC .............. *A61B 2017/00433* (2013.01); *A61B 2017/00438* (2013.01); *A61B 2017/2837* (2013.01)

(58) Field of Classification Search
CPC . A61B 17/2841; A61B 17/29; A61B 17/2909; A61B 17/320016
USPC ............... 606/144, 147, 148, 170, 174, 205
See application file for complete search history.

(56) References Cited

U.S. PATENT DOCUMENTS

| | | | |
|---|---|---|---|
| 3,120,847 A | 2/1964 | Cavaness | 606/147 |
| 3,407,816 A * | 10/1968 | Curutchet | A61B 17/3201 606/1 |
| 4,140,124 A * | 2/1979 | Curutchet | A61B 17/2841 30/194 |
| 4,189,831 A * | 2/1980 | Sonntag | B26B 13/12 30/232 |
| 4,226,241 A | 10/1980 | Walker | 606/207 |
| 4,491,135 A | 1/1985 | Klein | 606/147 |
| 4,827,929 A | 5/1989 | Hodge | 606/139 |
| 4,949,717 A | 8/1990 | Shaw | 606/147 |
| 5,176,696 A * | 1/1993 | Saunders | A61B 17/3201 30/340 |
| 5,219,354 A * | 6/1993 | Choudhury | A61B 17/0644 606/142 |
| 5,257,999 A | 11/1993 | Slanetz | 606/147 |
| 5,304,185 A | 4/1994 | Taylor | 606/147 |
| 5,364,409 A | 11/1994 | Kuwabara et al. | 606/148 |
| 5,478,345 A | 12/1995 | Stone et al. | 606/144 |
| 5,556,402 A | 9/1996 | Xu | 606/147 |
| 5,562,686 A | 10/1996 | Sauer et al. | 606/144 |
| 5,568,698 A * | 10/1996 | Harding | A01K 97/00 362/119 |
| 5,569,164 A | 10/1996 | Lurz | 600/158 |
| 5,578,048 A | 11/1996 | Pasqualucci et al. | 606/192 |
| 5,582,617 A | 12/1996 | Klieman et al. | 606/170 |
| 5,591,181 A | 1/1997 | Stone et al. | 606/144 |
| 5,601,575 A | 2/1997 | Measamer et al. | 606/147 |
| 5,609,601 A | 3/1997 | Kolesa et al. | 606/170 |
| 5,632,751 A | 5/1997 | Piraka | 606/139 |
| 5,632,752 A | 5/1997 | Buelna | 606/144 |
| 5,643,294 A | 7/1997 | Tovey et al. | 606/148 |
| 5,662,663 A | 9/1997 | Shallman | 606/144 |
| 5,674,230 A | 10/1997 | Tovey et al. | 606/139 |
| 5,702,407 A | 12/1997 | Kaji | 606/139 |
| 5,707,379 A | 1/1998 | Fleenor et al. | 606/145 |
| 5,951,587 A | 9/1999 | Qureshi et al. | 606/207 |
| 5,993,466 A | 11/1999 | Yoon | 606/147 |
| 6,017,358 A | 1/2000 | Yoon et al. | 606/205 |
| 6,071,289 A | 6/2000 | Stefanchik et al. | 606/147 |
| 6,159,233 A | 12/2000 | Matsuzawa | 606/223 |
| 6,249,977 B1 * | 6/2001 | Knoop | B26B 13/24 30/232 |
| D485,149 S * | 1/2004 | Sprouse | D8/107 |
| 6,883,238 B1 * | 4/2005 | Tran | B26B 13/20 30/232 |
| 2003/0004523 A1 | 1/2003 | Chan et al. | 606/148 |
| 2004/0093020 A1* | 5/2004 | Sinton | A61B 17/2816 606/208 |
| 2007/0023305 A1 | 2/2007 | Chan et al. | 206/366 |
| 2012/0253364 A1* | 10/2012 | Perin | A61B 17/2841 606/148 |
| 2012/0289975 A1 | 11/2012 | Martin et al. | 606/147 |

FOREIGN PATENT DOCUMENTS

| | | |
|---|---|---|
| EP | 0858777 | 5/2003 |
| WO | WO 2005/092207 | 10/2005 |
| WO | WO 2007/022928 | 3/2007 |
| WO | WO 2010/084322 | 7/2010 |

OTHER PUBLICATIONS

CS Surgical, Inc., http://www.cssurgical.com/needle-holders.html, Accessed: Sep. 25, 2015.
Scalan International, http://www.scanlaninternational.com/instrumentation/vats-mics/needle-holders/. Accessed: Sep. 25, 2015.

* cited by examiner

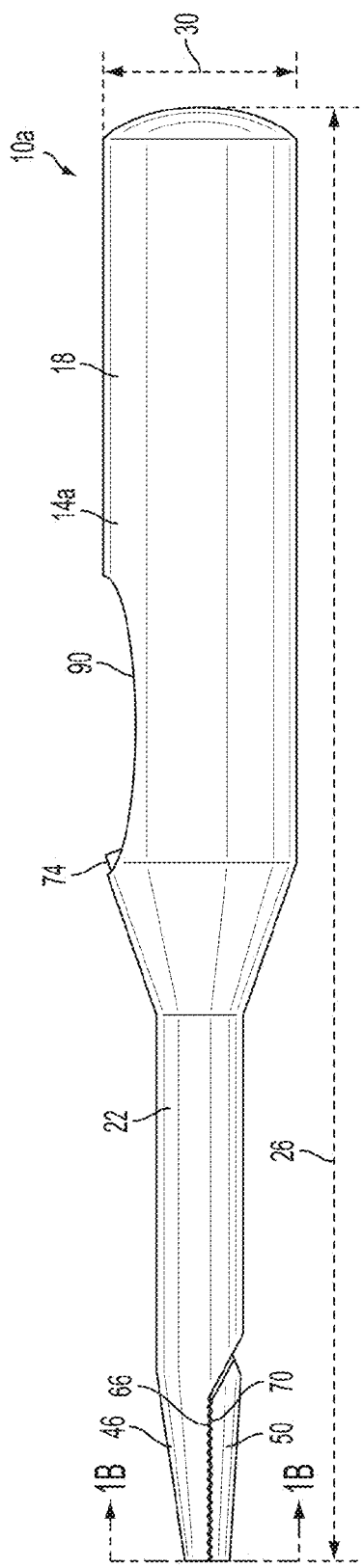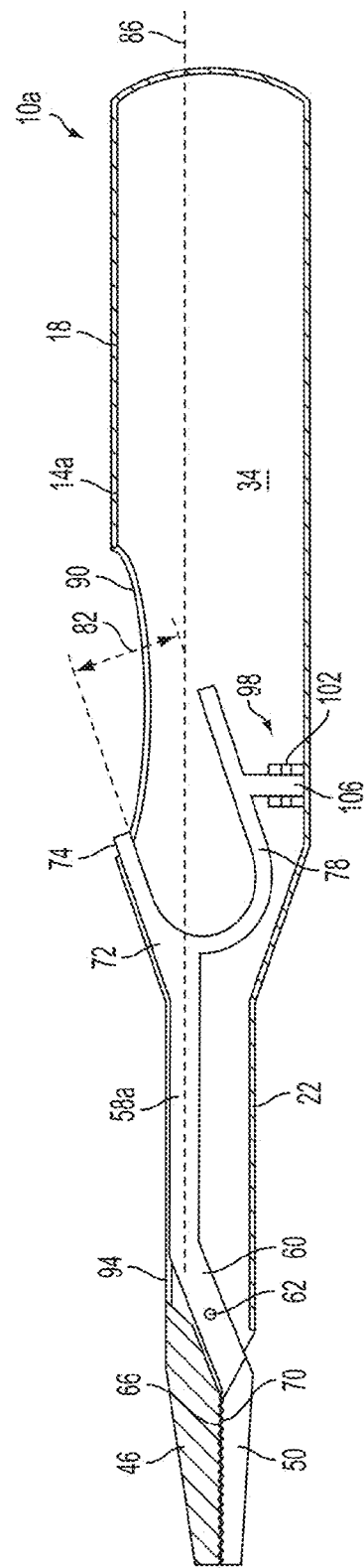

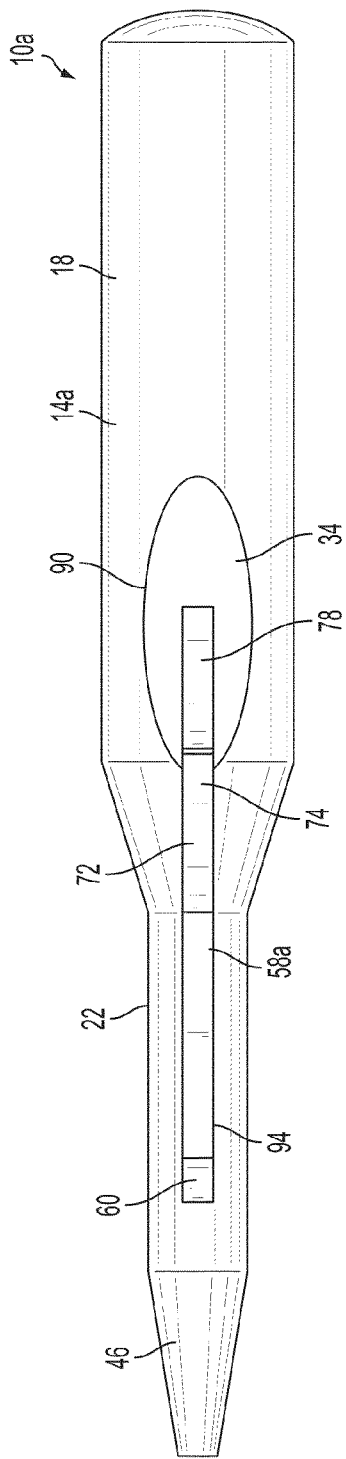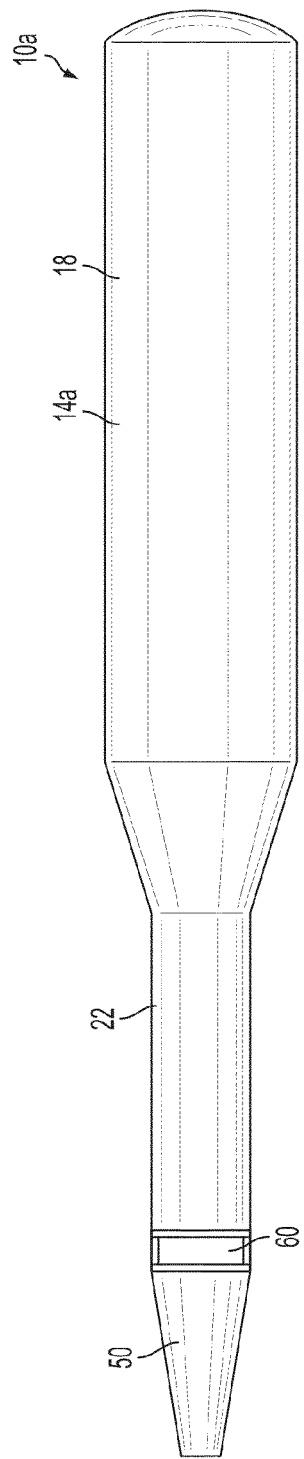
FIG. 1C
FIG. 1D

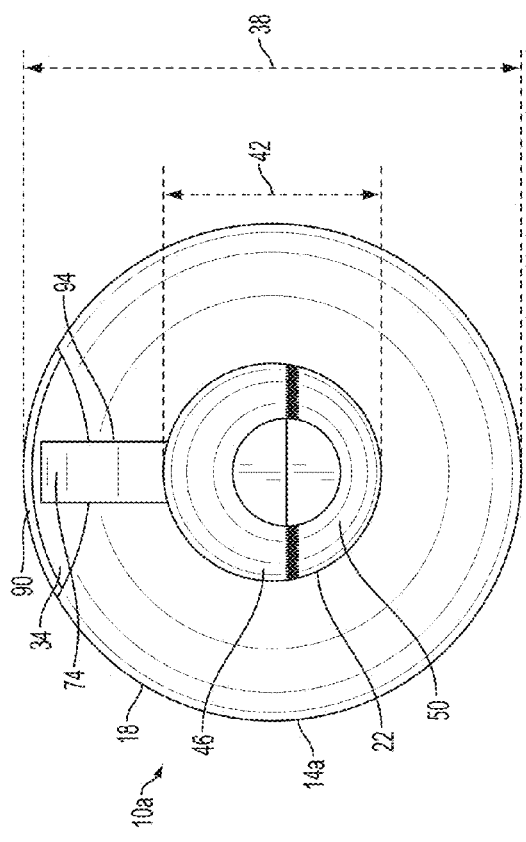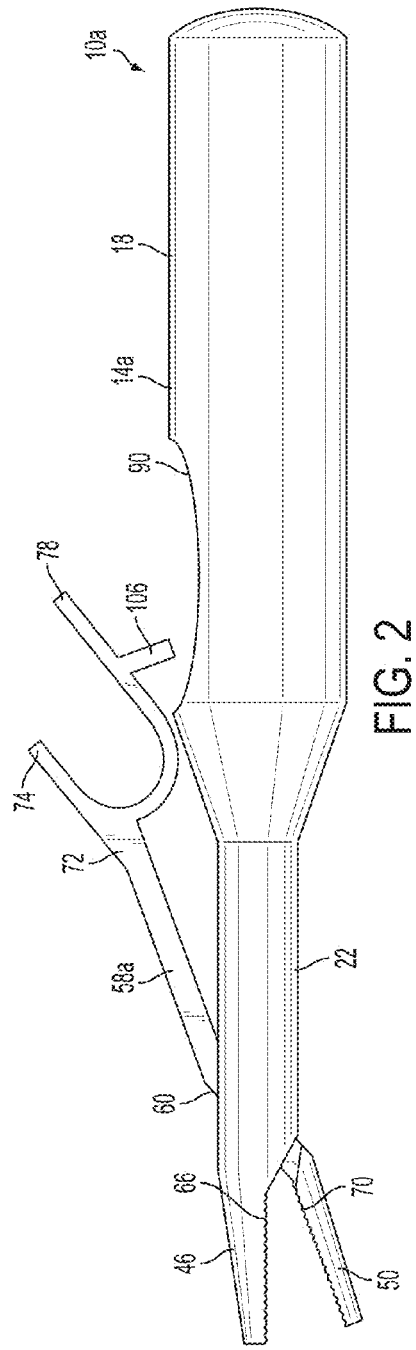

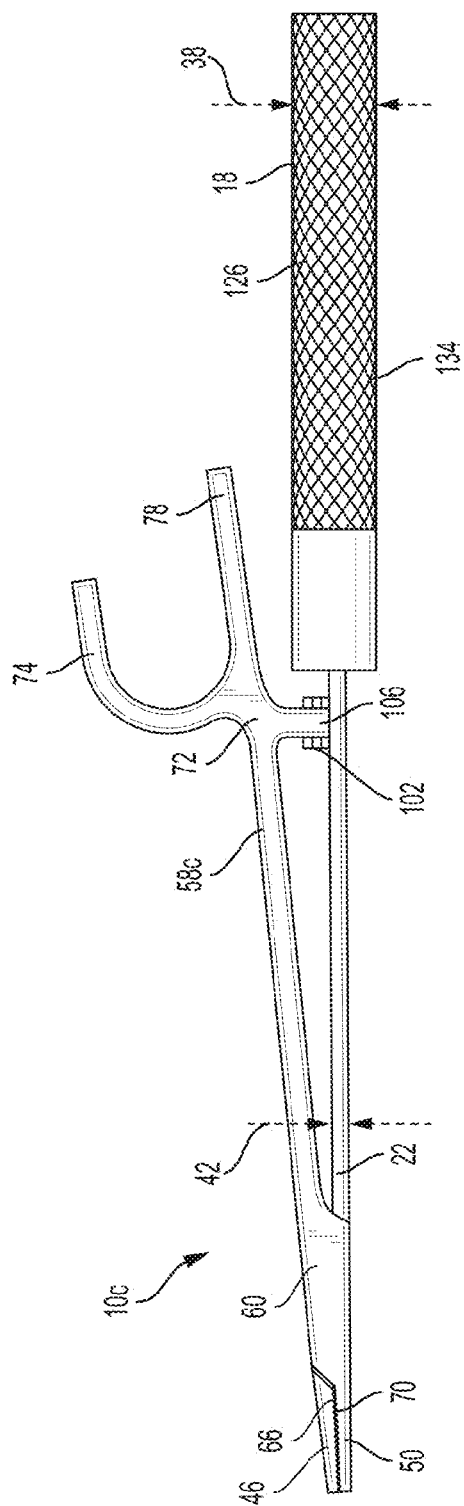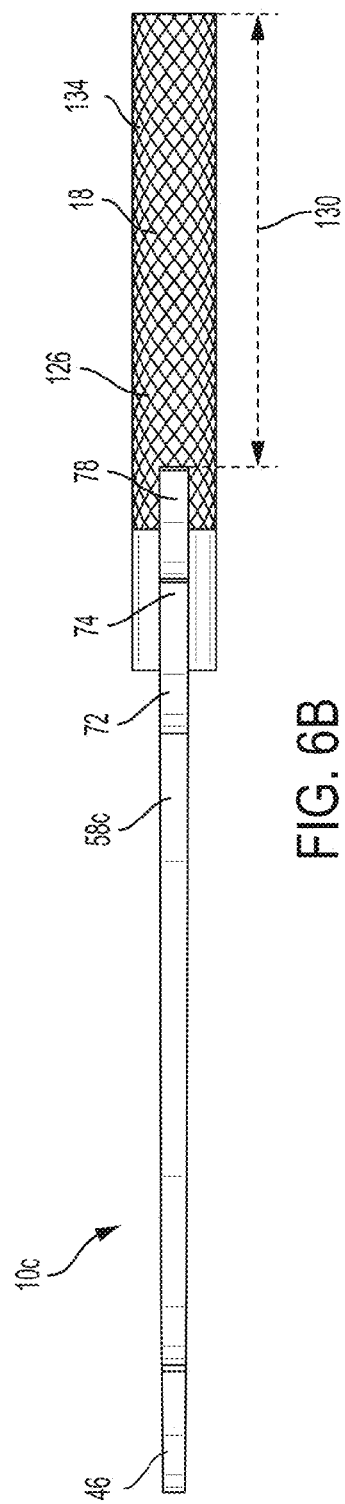

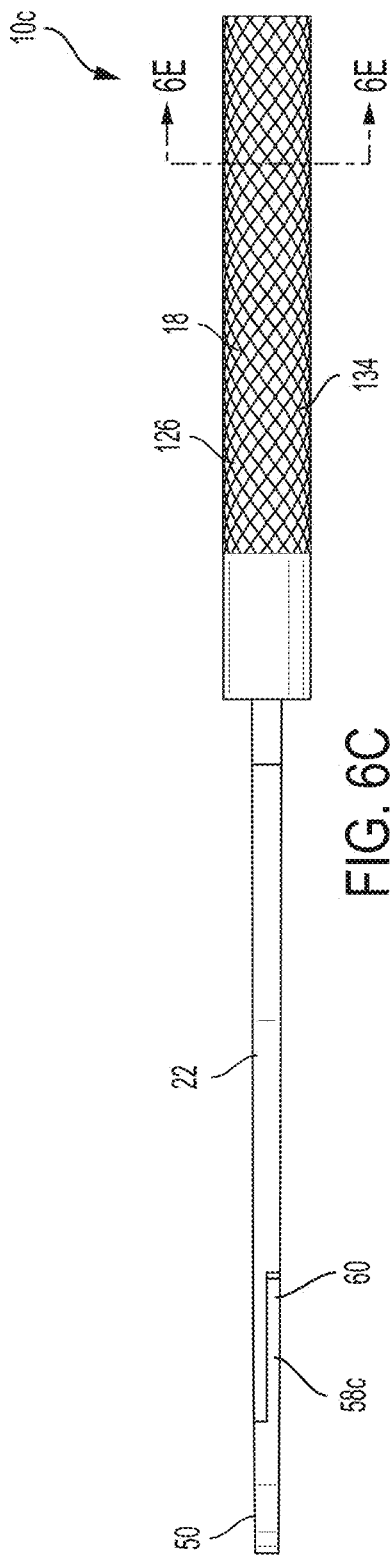

GRASPING APPARATUSES FOR HOLDING NEEDLES AND RELATED METHODS

CROSS-REFERENCE TO RELATED APPLICATION

This application claims priority to U.S. Provisional Patent Application No. 62/040,003, Filed Aug. 21, 2014, which is incorporated by reference in its entirety.

BACKGROUND

1. Field of Invention

The present invention relates generally to grasping devices, and more specifically, but not by way of limitation, to needle holders for grasping and/or securing a needle (e.g., during a suturing procedure).

2. Description of Related Art

Grasping apparatuses, and in particular, needle holders, may serve a variety of purposes. For example, a user (e.g., a clinician) may use a needle holder during a suturing procedure to manipulate a needle and/or to prevent the needle from inadvertently slipping relative to the user's hand.

A conventional needle holder may include handles resembling those of a traditional scissors or forceps. Typically, such handles terminate in one or more rings, which can be configured to receive a user's fingers such that relative movement of the user's fingers disposed within the rings selectively opens or closes jaws of the needle holder.

Examples of needle holders are disclosed in (1) U.S. Pat. No. 5,562,686; and (2) U.S. Pat. No. 6,071,289.

SUMMARY

Conventional needle holders may be capable of holding a needle; however, conventional handles can be cumbersome, particularly in space-restricted areas. For example, a user may be unable to rotate the needle holder due to interferences caused by rings on the handles. And, where space is limited, a user's hand and/or fingers may become decoupled from the handles during rotation of the needle holder, which may complicate certain procedures. Additionally, conventional needle holders may not adequately allow a user to exert sufficient torque on the needle holder to perform certain procedures.

Some embodiments of the present needle holders comprise: an elongated housing having a proximal portion and a distal portion; a first jaw member coupled to the distal portion of the housing; a second jaw member pivotally coupled to the first jaw member; and a lever pivotally coupled to the housing and coupled to the second jaw member such that the lever can be actuated by a user's thumb to selectively open and close the jaw members; where the housing defines an interior volume configured to receive at least a portion of the lever when the jaw members are closed. In some embodiments, the first jaw member is fixed relative to the housing. In some embodiments, the first jaw member is unitary with at least a portion of the housing.

In some embodiments of the present needle holders, the second jaw member is fixed relative to the lever. In some embodiments, the second jaw member is unitary with at least a portion of the lever. In some embodiments, the interior volume is configured to receive a majority of the lever when the jaw members are closed. In some embodiments, a majority of the lever is contained within a cross-sectional perimeter of the housing when the jaw members are closed.

Some embodiments of the present needle holders further comprise: a releasable locking mechanism configured to selectively resist opening of the jaw members when the jaw members are closed. In some embodiments, at least a portion of the releasable locking mechanism is disposed within the interior volume of the housing. In some embodiments, the releasable locking mechanism comprises a plurality of ratcheting teeth. In some embodiments, at least a portion of the releasable locking mechanism is disposed on the lever. In some embodiments, the lever comprises a protrusion that extends from the housing when the jaw members are closed, the protrusion configured to be actuated by a user's thumb to actuate the releasable locking mechanism.

In some embodiments of the present needle holders, the proximal portion of the housing has a first transverse dimension, the distal portion of the housing has a second transverse dimension, and the first transverse dimension is larger than the second transverse dimension. In some embodiments, the housing tapers in transverse dimension from the proximal portion to the distal portion. In some embodiments, the housing comprises a substantially circular cross-section. In some embodiments, the housing defines an opening in communication with the interior volume, the opening configured to receive at least a portion of the user's thumb when the jaw members are closed. In some embodiments, the proximal portion of the housing defines a handle.

In some embodiments of the present needle holders, the distal portion of the housing is angularly disposed at a non-parallel angle relative to the proximal portion of the housing. In some embodiments, a longitudinal axis of the distal portion is angularly disposed at a non-parallel angle relative to a longitudinal axis of the proximal portion. In some embodiments, a longitudinal axis of the lever extends through the proximal portion of the housing when the jaw members are closed. In some embodiments, the distal portion of the housing defines a depression configured to receive a finger of the user. In some embodiments, at least a portion of the depression defines a gripping surface. In some embodiments, the housing is ringless.

Some embodiments of the present needle holders comprise: an elongated handle having a proximal portion and a distal portion; a first jaw member coupled to the distal portion of the handle; a second jaw member pivotally coupled to the first jaw member; and a lever pivotally coupled to the handle and coupled to the second jaw member; where the handle extends proximally beyond the lever such that the lever can be actuated by a user's thumb to selectively open and close the jaw members while the handle is grasped within the user's hand. In some embodiments, the handle extends proximally beyond the lever a distance of at least 5 centimeters (cm) when the jaw members are closed. In some embodiments, the proximal portion of the handle comprises a substantially constant cross-section. In some embodiments, the proximal portion of the handle comprises a substantially circular cross-section. In some embodiments, the proximal portion of the handle defines a gripping surface. In some embodiments, the first jaw member is fixed relative to the handle. In some embodiments, the first jaw member is unitary with at least a portion of the handle.

In some embodiments of the present needle holders, the second jaw member is fixed relative to the lever. In some embodiments, the second jaw member is unitary with at least a portion of the lever.

Some embodiments of the present needle holders further comprise: a releasable locking mechanism configured to selectively resist opening of the jaw members when the jaw members are closed. In some embodiments, at least a portion of the releasable locking mechanism is disposed on the lever. In some embodiments, releasable locking mechanism comprises a plurality of ratcheting teeth.

In some embodiments of the present needle holders, the proximal portion of the handle has a first transverse dimension, the distal portion of the handle has a second transverse dimension, and the first transverse dimension is larger than the second transverse dimension. In some embodiments, the handle is ringless. In some embodiments, the lever is ringless. In some embodiments, a proximal portion of the lever defines a pair of opposing concave surfaces configured to receive the user's thumb.

Some embodiments of the present methods (e.g., for for grasping with a needle holder) comprise: gripping a proximal portion of a housing having a distal portion coupled to a first jaw member; and actuating a lever pivotally coupled to the housing and coupled to a second jaw member to selectively open and close the jaw members; where the housing defines an interior volume configured to receive at least a portion of the lever when the jaw members are closed. Some embodiments further comprise: locking at least a portion of the lever relative to the housing and within the interior volume of the housing.

Some embodiments of the present methods (e.g., for grasping with a needle holder) comprise: grasping, within a hand, a proximal portion of a handle having a distal portion coupled to a first jaw member; and actuating, with a thumb of the hand, a lever pivotally coupled to the handle and coupled to a second jaw member to selectively open and close the jaw members; where the handle extends proximally beyond the lever. Some embodiments further comprise: grasping a needle between the jaw members.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

Further, a device or system that is configured in a certain way is configured in at least that way, but it can also be configured in other ways than those specifically described.

The terms "comprise" (and any form of comprise, such as "comprises" and "comprising"), "have" (and any form of have, such as "has" and "having"), "include" (and any form of include, such as "includes" and "including"), and "contain" (and any form of contain, such as "contains" and "containing") are open-ended linking verbs. As a result, an apparatus that "comprises," "has," "includes," or "contains" one or more elements possesses those one or more elements, but is not limited to possessing only those elements. Likewise, a method that "comprises," "has," "includes," or "contains" one or more steps possesses those one or more steps, but is not limited to possessing only those one or more steps.

Any embodiment of any of the apparatuses, systems, and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Some details associated with the embodiments are described above and others are described below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The figures are drawn to scale (unless otherwise noted), meaning the sizes of the depicted elements are accurate relative to each other for at least the embodiment depicted in the figures.

FIG. 1A is a side view of a first embodiment of the present needle holders, shown in a closed configuration.

FIG. 1B is a partially cross-sectional side view of the needle holder of FIG. 1A.

FIGS. 1C-1E are top, bottom, and front views, respectively, of the needle holder of FIG. 1A.

FIG. 2 is a side view of the needle holder of FIG. 1A, shown in an open configuration.

FIG. 6A is a side view of a third embodiment of the present needle holders, shown in a closed configuration.

FIGS. 6B-6D are top, bottom, and front views, respectively, of the needle holder of FIG. 6A.

FIG. 6E is a cross-sectional front view of the needle holder of FIG. 6A.

DETAILED DESCRIPTION OF ILLUSTRATIVE EMBODIMENTS

Figure 3:
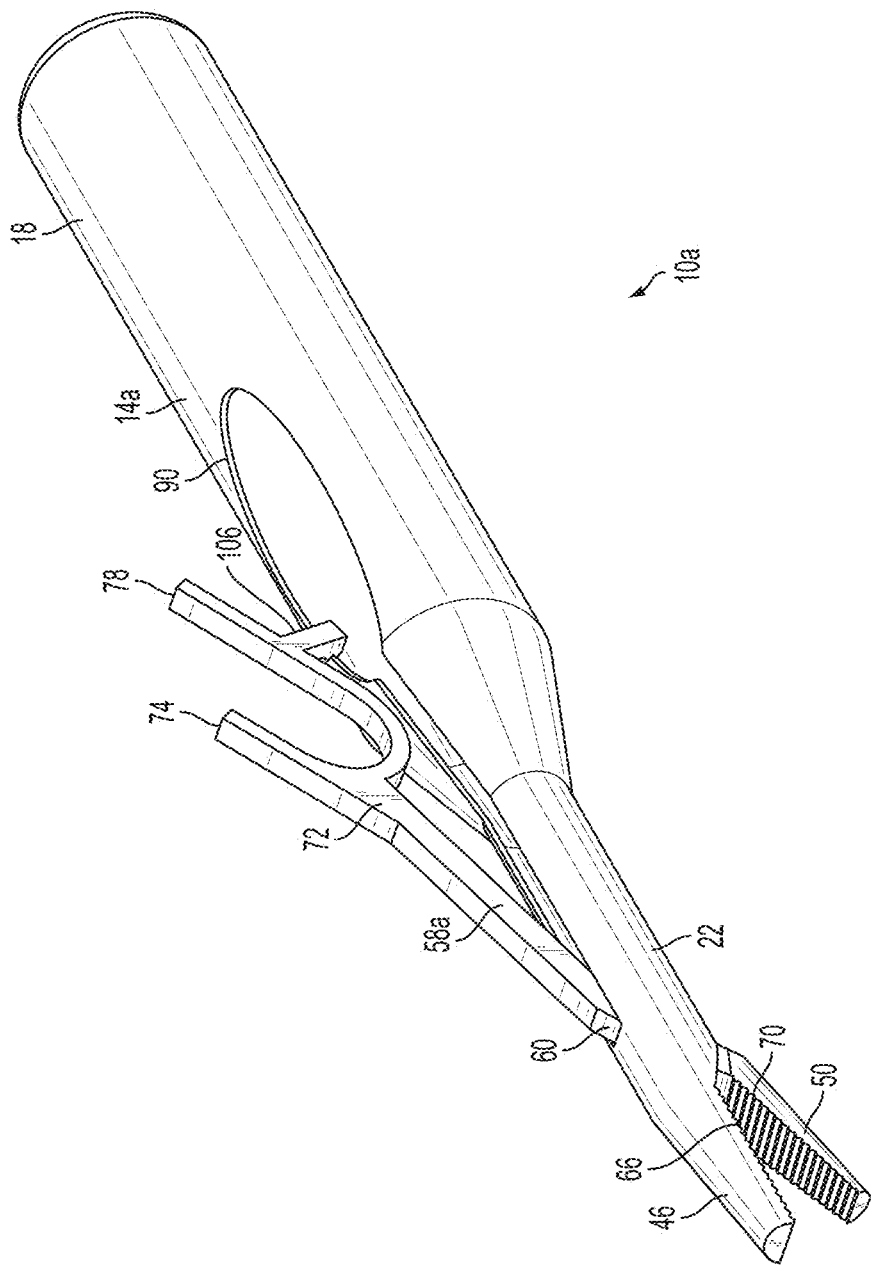
FIG. 3 is a perspective view of the needle holder of FIG. 2.

Referring now to the drawings and more particularly to FIGS. 1A-1E, 2, and 3, shown therein and designated by the reference numeral 10a is a first embodiment of the present needle holders. In the embodiment shown, holder 10a comprises an elongated housing 14a having a proximal portion 18 and a distal portion 22 that is smaller than the proximal portion, as shown. In this embodiment, housing 14a is elongated in that it has a length 26 (as shown, including first jaw member 46) that is between 5 to 10 times (e.g., about 8 times) a maximum transverse dimension 30 of the housing. In the embodiment shown, proximal portion 18 defines a handle (e.g., is configured to be grasped by a user in a manner similar to grasping a screw driver, for example, housing 14a is ringless). In this embodiment, housing 14a defines an interior volume 34 (FIG. 1B). And, in this embodiment, housing 14a of holder 10a is substantially hollow; however, in other embodiments, housing 14a may be only partially hollow, such as, for example, defining an interior volume 34 in such a way as to balance the needle holder (e.g., by distributing weight) within a user's hand (e.g., to reduce and/or minimize any tendency to tip due to gravity when held in an operative position by a user).

In the embodiment shown, housing 14a comprises a substantially circular cross-section (FIG. 1E). In this embodiment, housing 14a tapers in transverse dimension from proximal portion 18 to distal portion 22. For example, proximal portion 18 of housing 14a has a first transverse dimension 38, distal portion 22 of the housing has a second transverse dimension 42, and the first transverse dimension is larger than the second transverse dimension, such as, for example, more than or between any two of: 10%, 50%, 100%, 150%, 200%, 250%, and/or 300% larger (approximately 230% larger, as in the depicted embodiment). In this way, for example, a user can exert adequate torque on the needle holder during rotation, due in part to the mechanical advantage provided by larger transverse dimension 38 of proximal portion 18, while smaller transverse dimension 42 of distal portion 22 can minimize physical interference with needle holder 10a, such as in space-restricted areas. Due in part to the substantially cylindrical, tapered, and slim-profile nature of housing 14a (e.g., which can function as a handle), needle holder 10a can facilitate greater mobility, control, access, and/or the like when, for example, suturing a wound.

In this embodiment, holder 10a comprises a first jaw member 46 coupled to distal portion 22 of housing 14a. In the embodiment shown, first jaw member 46 is fixed relative to (e.g., or is unitary with and/or forms part of) housing 14a. However, in other embodiments, first jaw member 46 may be pivotally coupled to housing 14a, and actuation of the first jaw member may be accomplished by one or more linkages, levers, and/or the like. In some embodiments, the first jaw member may be removably coupled to housing 14a to facilitate replacement and/or adjustment (e.g., to configure the needle holder to receive needles of different sizes).

In the embodiment shown, holder 10a comprises a second jaw member 50 pivotally coupled to first jaw member 46 and coupled to a lever 58a. In this embodiment, for example, second jaw member 50 is fixed relative to (e.g., or is unitary with and/or forms part of) lever 58a, which is pivotally coupled to distal portion 22 of housing 14a (e.g., and thus first jaw member 46) via a pin 62, which, as shown, may extend into interior volume 34 and into and/or through a portion 60 of lever 58a. In other embodiments, second jaw member 50 may be pivotally coupled to lever 58a and/or housing 14a, and actuation of the second jaw member may be accomplished by one or more levers, linkages and/or the like between second jaw member 50, first jaw member 46, lever 58a, and/or housing 14a. In some embodiments, the second jaw member may be removably coupled to lever 58a and/or housing 14a to facilitate replacement and/or adjustment of the jaw member (e.g., to configure the needle holder to receive needle of different sizes).

In the embodiment shown, the first and second jaw members each comprise a gripping surface 66 or 70, respectively, which can be configured to grasp an object (e.g., a needle). For example, in this embodiment, gripping surfaces 66 and 70 are serrated or ridged; however, in other embodiments, the gripping surfaces can comprise any suitable texture (e.g., may be smooth, comprise one or more grooves, and/or the like), and gripping surface 66 need not comprise the same texture as gripping surface 70. In this embodiment, gripping surface 66 is substantially coincident to gripping surface 70 when the jaw members are fully closed (e.g., substantially all of each gripping surface rests against the other); however, in other embodiments, the jaw members and/or gripping surfaces may define one or more openings when the jaw members are fully closed. Other embodiments of the present needle holders can comprise any suitable jaw members in any suitable configuration.

As described above, in this embodiment, lever 58a is pivotally coupled to housing 14a (at a portion 60, via pin 62). In the embodiment shown, the pivotal coupling between housing 14a and lever 58a (e.g., and thus their respective jaw members 46 and 50) is substantially unrestrained (e.g., with the exception of frictional forces, such as between pin 62 and lever 58a). In other embodiments, the present devices may include a biasing member (e.g., a spring). For example, a spring can be disposed between lever 58a and housing 14a, or between first jaw member 46 and second jaw member 50 to bias the jaw members towards an open or a closed position.

In the embodiment shown, lever 58a can be actuated by a user's thumb to selectively open and close the jaw members (e.g., when the user is grasping proximal portion 18). In this embodiment, lever 58a, at an end opposite second jaw member 50, includes a generally u-shaped end portion 72, which can be sized to receive a user's thumb (e.g., lever 58a is ringless). For further example, in this embodiment, portion 72 comprises a first protruding portion 74 coupled to a second protruding portion 78, a portion of which is spaced from a portion of the first protruding portion at a distance 82, where each protruding portion extends in generally a same direction away from second jaw member 50 (e.g., however, the first and second protruding portions need not be linear and need not be parallel with one another). In this embodiment, distance 82 can be sized such that portion 72 is configured to receive a user's thumb (e.g., where distance 82 generally corresponds to an expected maximum thickness of a human thumb). In this way, when a user places their thumb within portion 72 and: (1) moves their thumb away from needle holder 10a, the user's thumb can contact first protruding portion 74 to pivot lever 58a away from housing 14a to cause jaw members 46 and 50 to open; and (2) moves their thumb towards needle holder 10a, the user's thumb can contact second protruding portion 78 to pivot lever 58a toward housing 14a to cause jaw members 46 and 50 to close.

In some embodiments, lever 58a and housing 14a are configured to coincide, meet, and/or intersect at more portions than just a pivot point (e.g., pin 62). For example, in embodiment shown, interior volume 34 of housing 14a is configured to receive at least a portion of (up to and including a majority and/or all of) lever 58a when jaw members 46 and 50 are closed. In this embodiment, when the jaw members are closed, lever 58a lies substantially within and is laterally centered relative to housing 14a (FIG. 1C), such that, for example, a longitudinal axis 86 of lever 58a (e.g., of a portion of the lever between portions 60 and 72) extends through proximal portion 18 of housing 14a. By way of further example, in this embodiment, when jaw members 46 and 50 are closed, at least a majority of lever 58a is contained within a cross-sectional perimeter of housing 14a (FIG. 1E).

In the embodiment shown, housing 14a of holder 10a defines an opening 90 and a slot 94, each in communication with the other and with interior volume 34, where the opening and/or slot are configured to allow portions of lever 58a to enter interior volume 34 when the jaw members are closed and/or are closing. In this embodiment, opening 90 is also configured to receive at least a portion of the user's thumb when the jaw members are closed and/or are closing (e.g., with a user's thumb disposed between protruding portions 74 and 78 of portion 72). As shown, when the jaw members are opened, lever 58a can extend out of housing (e.g., through slot 94 and/or opening 90, as shown in FIG. 2).

For example, in the embodiment shown, holder 10a comprises a releasable locking mechanism 98 configured to selectively resist opening of the jaw members when the jaw members are closed. In this embodiment, releasable locking mechanism 98 comprises a first portion 102 and a second portion 106, each having one or more ratcheting teeth (e.g., as shown). In mechanism 98, first portion 102 is coupled to housing 14a and is disposed within interior volume 34 (e.g., is embedded within the housing) and second portion 106 is coupled to lever 58a and extends at a non-parallel angle away from the lever in a direction into interior volume 34. In this way, at least a portion of (e.g., up to and including all of) locking mechanism 98 can be disposed within housing 14a, for example, to maintain a slim profile of the needle holder and/or to minimize interferences caused by the needle holder during use.

In the embodiment shown, as lever 58a is moved to a closed position, second portion 106 can contact first portion 102 and ratcheting teeth of each portion can engage with one another to releasably secure a position of lever 58a relative to housing 14a (e.g., and thus a position of first jaw member 46 relative to second jaw member 50). As shown, the number and/or range of releasably lockable positions of lever 58a relative to housing 14a can be adjusted, for example, by increasing the length of the first and/or second portions of locking mechanism 98, and/or by adjusting the number, relative position of, and/or the like of ratcheting teeth of the first and/or second portions of the locking mechanism, and/or the like.

In this embodiment, mechanism 98 is configured to releasably retain the jaw members relative to each other. For example, in the depicted embodiment, lever 58a comprises a protrusion (e.g., a portion of first protruding portion 74) that extends from housing 14a (e.g., through opening 90 and/or slot 94, as shown) when the jaw members are closed. In the embodiment shown, first protruding portion 74 is configured to be actuated by a user's thumb to release mechanism 98 and/or pivot lever 58a relative to housing 14a to selectively open or close the jaw members (e.g., whether or not a user's thumb is disposed between protruding portions 74 and 78 and/or within interior volume 34). For example, if a lateral force is applied to the first protruding portion, one or more ratcheting teeth of first portion 102 and/or second portion 106 can be moved together (e.g., into to a locked configuration) or apart (e.g., out of a locked configuration or into an unlocked configuration). In some embodiments, lever 58a can be biased (e.g., via a spring) to a locked or unlocked position. As shown, even though first protruding portion 74 extends from housing 14a, the first protruding portion may still be contained within a cross-sectional perimeter of housing 14a and/or needle holder 10a (FIG. 1E). Other embodiments of the present needle holders can comprise any suitable locking mechanisms.

Some embodiments of the present methods for grasping with a needle holder comprise gripping a proximal portion (e.g., 18) of a housing (e.g., 14a) having a distal portion (e.g., 22) coupled to a first jaw member (e.g., 46) and actuating a lever (e.g., 58a) pivotally coupled to the housing and coupled to a second jaw member (e.g., 50) to selectively open (e.g., as shown in FIG. 2) and close (e.g., as shown in FIG. 1A) the jaw members, where the housing defines an interior volume (e.g., 34) configured to receive at least a portion of the lever when the jaw members are closed. Some methods comprise locking (e.g., with releasable locking mechanism 98) at least a portion of the lever relative to the housing and within the interior volume of the housing. Some methods comprise grasping a needle between the jaw members.

Figure 4A:
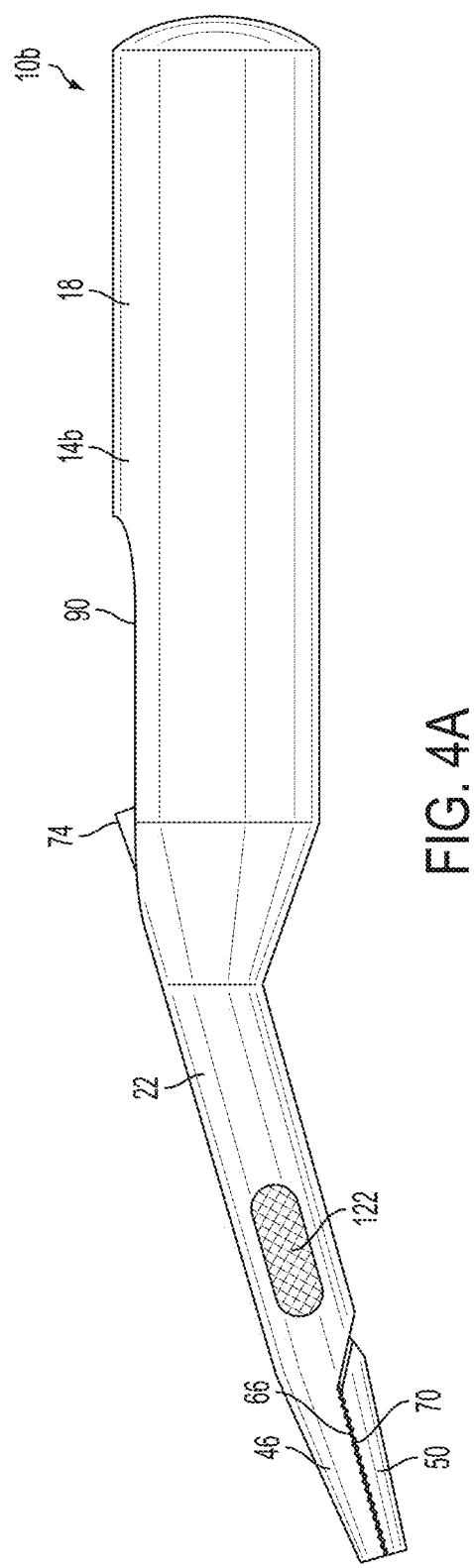
FIG. 4A is a side view of a second embodiment of the present needle holders, shown in a closed configuration.
Figure 4B:
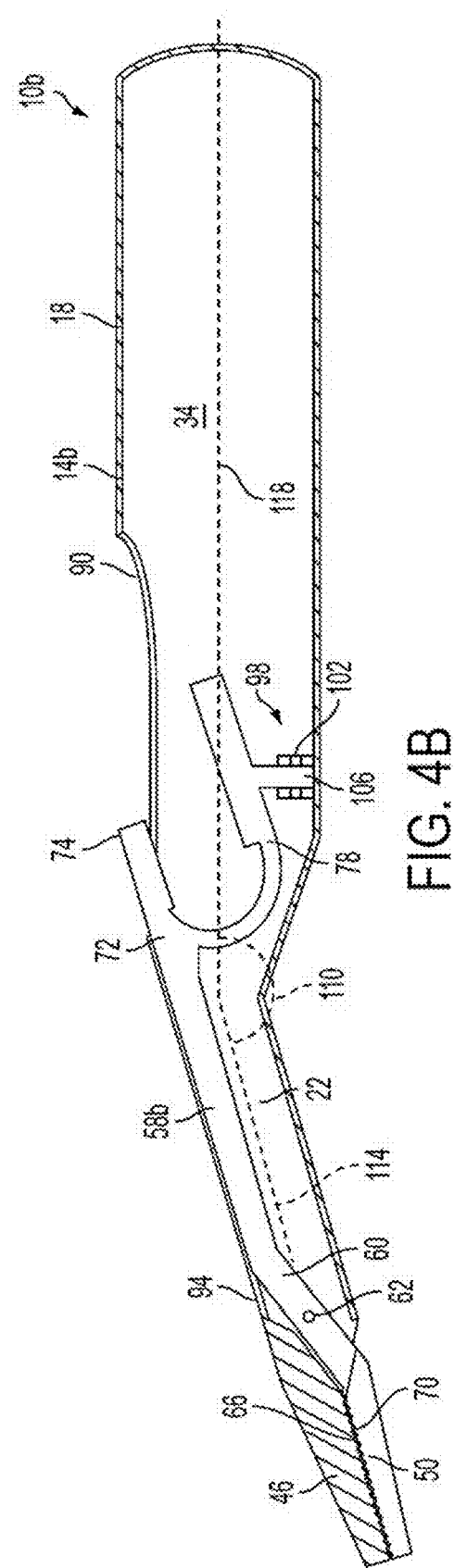
FIG. 4B is a partially cross-sectional side view of the needle holder of FIG. 4A.
Figure 5:
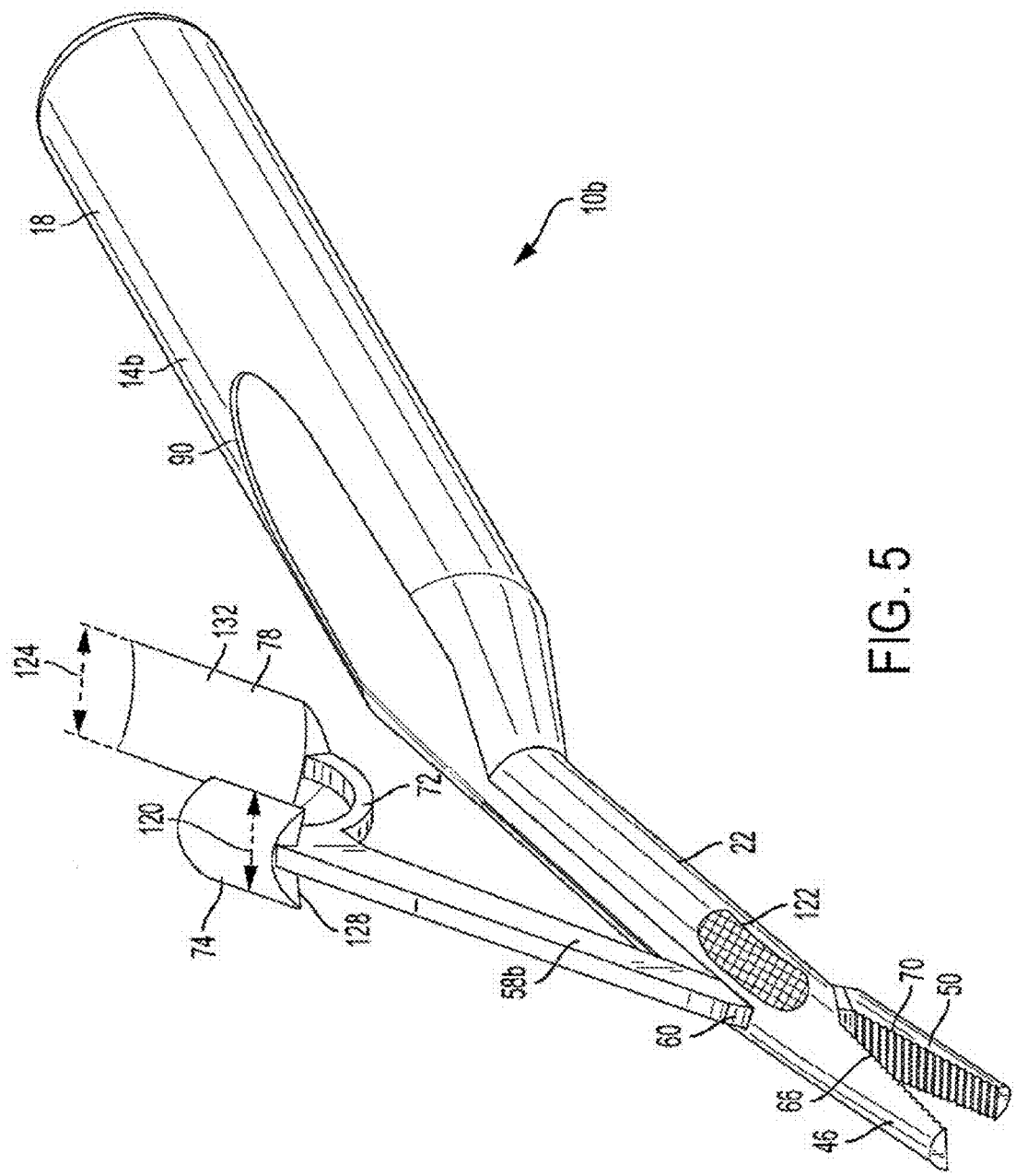
FIG. 5 is a perspective view of the needle holder of FIG. 4A, shown in an open configuration.

Referring now to FIGS. 4A, 4B, and 5, shown therein and designated by the reference numeral 10b is a second embodiment of the present needle holders. Holder 10b is substantially similar to holder 10a, with the primary exceptions described below. While the following features are described with respect to holder 10b, any and/or all of the following features may be applied to other embodiments of the present needle holders (e.g., a housing 14b including a distal portion 22 that is angularly disposed at a non-parallel angle 110 relative to a proximal portion 18 of the housing, a lever 58b having a first protruding portion 74 and a second protruding portion 78, each defining one of a set of concave surfaces, 128 and 132, respectively, a housing 14b having a distal portion 22 defining a depression 122, and/or the like, may be applied to needle holders 10a, 10c, and/or the like). In the embodiment shown, distal portion 22 of housing 14b is angularly disposed at a non-parallel angle (e.g., 110) relative to proximal portion 18 of the housing (e.g., and lever 58b varies from lever 58a, accordingly). For example, in this embodiment, a longitudinal axis 114 of distal portion 22 is angularly disposed at a non-parallel angle (e.g., 110) relative to a longitudinal axis 118 of proximal portion 18. In at least this way, housing 14b may physically inhibit holder 10b from rolling when the holder is placed on an (e.g., uneven) surface, provide for enhanced ergonomics of the holder, and/or the like.

In the depicted embodiment, first protruding portion 74 and second protruding portion 78 of lever 58b each have a maximum transverse dimension, 120 and 124, respectively, such that portions of generally u-shaped end portion 72 are wider than other portions of lever 58b between portion 72 and second jaw member 50 (FIG. 5). In the embodiment shown, first protruding portion 74 and second protruding portion 78 each are configured to extend laterally around a portion of a user's thumb when the user's thumb is disposed between the first and second protruding portions. For example, in this embodiment, first protruding portion 74 and second protruding portion 78 each define one of opposing concave surfaces, 128 and 132, respectively, where each concave surface is configured to receive a user's thumb (e.g., and one or both concave surfaces may be textured). In these ways and others, lever 58b may provide an increased surface area for contacting a user's thumb, provide resistance to the user's thumb from inadvertently sliding laterally out from between first protruding portion 74 and second protruding portion 78, and/or the like. In the embodiment shown, opposing concave surfaces 128 and 132 are spaced apart from one another (e.g., such that, if desired, a user's thumb may be removed laterally from between first protruding portion 74 and second protruding portion 78).

In the depicted embodiment, distal portion 22 of housing 14b defines a depression 122, which may be configured to receive a user's finger (e.g., a user's index finger) (e.g., when the holder is held in an operative position). In the embodiment shown, at least a portion of depression 122 defines an (e.g., textured) gripping surface. In at least these ways, depression 122 of distal portion 22 may provide for enhanced control by a user over holder 10b (e.g., when manipulating the holder, for example, during a suturing procedure).

Referring now to FIGS. 6A-6E, shown therein and designated by the reference numeral 10c is a third embodiment of the present needle holders. Holder 10c is substantially similar to holder 10a, with the primary exception being that holder 10c comprises an elongated handle 126 in lieu of a housing (e.g., 14a), where the handle has a distal portion 22 and a proximal portion 18 (e.g., which may define a gripping surface 134, as shown). In at least this way, holder 10c (e.g., via absence of a housing) may facilitate sterilization of the holder. Otherwise, holder 10c may possess any and/or all of the features described above for holders 10a and/or 10b. While the following features are described with respect to holder 10c, any and/or all of the following features may be applied to other embodiments of the present needle holders (e.g., a handle 126 (or a housing) extending proximally beyond a lever 58c may be applied to needle holders 10a, 10b, and/or the like).

In the embodiment shown, handle 126 extends proximally beyond lever 58c such that the lever can be actuated by a user's thumb to selectively open and close jaw members 46 and 50 while the handle, and particularly a proximal portion 18 thereof, is grasped within the user's hand. For example, in this embodiment, handle 126 extends in a proximal direction (e.g., in a direction from distal portion 22 towards proximal portion 18) beyond lever 58c a distance 130 when jaw members 46 and 50 are closed. In the depicted embodiment, distance 130 is at least 5 centimeters (cm). However, in other embodiments, handle 126 may extend proximally beyond lever 58c by any suitable distance, such as, for example, between any two of or greater than any one of 3.0, 3.5, 4.0, 4.5, 5.0, 5.5, 6.0, 6.5, 7.0, 7.5, 8.0, 8.5, 9.0, 9.5, and 10 cm.

For example, some embodiments of the present methods for grasping a needle with a needle holder (e.g., 10c) comprise grasping, within a hand, a proximal portion (e.g., 18) of a handle (e.g., 126) having a distal portion (e.g., 22) coupled to a first jaw member (e.g., 46), and actuating, with a thumb of the hand, a lever (e.g., 58c) pivotally coupled to the handle and coupled to a second jaw member (e.g., 50) to selectively open and close the jaw members, where the handle extends proximally beyond the lever (e.g., by a distance 130).

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the methods and systems are not intended to be limited to the particular forms disclosed. Rather, they include all modifications and alternatives falling within the scope of the claims, and embodiments other than the one shown may include some or all of the features of the depicted embodiment. For example, elements may be omitted or combined as a unitary structure, and/or connections may be substituted. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A needle holder comprising:
   an elongated handle having a proximal portion and a distal portion, the proximal portion defining a gripping surface and having a length and a width, and where the gripping surface defines a cross-sectional perimeter of the proximal portion of the elongated handle;
   a first jaw member coupled to the distal portion of the handle;
   a second jaw member pivotally coupled to the first jaw member along an axis that is parallel to the width of the proximal portion of the handle;
   a lever pivotally coupled to the handle and coupled to the second jaw member, a proximal portion of the lever including a first protruding portion that extends proximally away from the first and second jaw members, and a second protruding portion that extends proximally away from the first and second jaw members, the first and second protruding portions spaced apart from each other to define a thumb recess that opens proximally away from the first and second jaw members, the thumb recess sized to receive a distal portion of a user's thumb; and
   a releasable locking mechanism configured to selectively resist opening of the jaw members when the jaw members are closed, the releasable locking mechanism comprising a first lock portion coupled to the elongated handle, a second lock portion coupled to the lever, and a plurality of teeth, where a first portion of the plurality of teeth is coupled to the first lock portion and a second portion of the plurality of teeth is coupled to the second lock portion;
   where the first lock portion is contained within the cross-sectional perimeter of the proximal portion of the elongated handle;
   where, when the first and second jaws are closed, the handle extends proximally beyond the lever such that the lever can be actuated by a user's thumb, when the user's thumb extends toward the first and second jaw members, to selectively open and close the jaw members while the gripping surface of the handle is grasped within the user's hand; and
   where, when the first and second jaws are closed, the width of the proximal portion of the handle along a majority of the length between the lever and a proximal end of the handle is larger than an average width of the handle between the most-proximal portion of the lever and the first jaw member.

2. The needle holder of claim 1, where the handle extends proximally beyond the lever a distance of at least 5 centimeters (cm) when the jaw members are closed.

3. The needle holder of claim 1, where the first jaw member is fixed relative to the handle.

4. The needle holder of claim 1, where the second jaw member is fixed relative to the lever.

5. The needle holder of claim 1, where the handle is ringless.

* * * * *